(12) United States Patent  (10) Patent No.: US 10,206,492 B2
Gottlieb  (45) Date of Patent: Feb. 19, 2019

(54) BRUSHES USEFUL FOR CLEANING TEETH AND INTERDENTAL SPACES

(71) Applicant: STEVI, LLC, Silver Spring, MD (US)

(72) Inventor: Ray M. Gottlieb, Silver Spring, MD (US)

(73) Assignee: STEVI, LLC, Chester, MD (US)

( * ) Notice: Subject to any disclaimer, the term of this patent is extended or adjusted under 35 U.S.C. 154(b) by 511 days.

(21) Appl. No.: 14/879,272

(22) Filed: Oct. 9, 2015

(65) Prior Publication Data
US 2017/0099940 A1    Apr. 13, 2017

(51) Int. Cl.
| A46B 9/02 | (2006.01) |
| A46B 9/04 | (2006.01) |
| A46B 13/02 | (2006.01) |
| A61C 15/00 | (2006.01) |
| A61C 17/34 | (2006.01) |
| A61C 17/24 | (2006.01) |

(52) U.S. Cl.
CPC ............ *A46B 9/026* (2013.01); *A46B 9/028* (2013.01); *A46B 9/04* (2013.01); *A46B 13/02* (2013.01); *A61C 15/00* (2013.01); *A61C 17/34* (2013.01); *A61C 17/3472* (2013.01); *A46B 2200/108* (2013.01); *A61C 17/24* (2013.01); *A61C 17/3463* (2013.01)

(58) Field of Classification Search
CPC ........... A46B 9/026; A46B 9/028; A46B 9/04; A46B 13/02; A61C 15/00; A61C 17/34
See application file for complete search history.

(56) References Cited

U.S. PATENT DOCUMENTS

| 4,603,448 A | 8/1986 | Middleton et al. |
| 5,071,348 A | 12/1991 | Woog |
| 5,145,369 A | 9/1992 | Lustig et al. |
| 5,499,420 A | 3/1996 | Boland |
| 5,535,474 A | 7/1996 | Salazar |
| 5,623,746 A * | 4/1997 | Ichiro .................. A61C 15/047 15/167.1 |
| 5,647,385 A | 7/1997 | Zebuhr |
| 5,732,433 A | 3/1998 | Gocking et al. |
| 5,850,655 A | 12/1998 | Gocking et al. |
| 6,106,290 A | 8/2000 | Weissman |
| 6,178,579 B1 | 1/2001 | Blaustein |
| 6,230,354 B1 | 5/2001 | Sproat |
| 6,237,178 B1 | 5/2001 | Krammer et al. |

(Continued)

FOREIGN PATENT DOCUMENTS

| EP | 1494610 B1 | 12/2007 | |
| WO | WO 2008072798 A2 * | 6/2008 | ............... A46B 9/04 |

OTHER PUBLICATIONS

US 6,598,254, 07/2003, Blaustein et al. (withdrawn)

(Continued)

*Primary Examiner* — Shay Karls
(74) *Attorney, Agent, or Firm* — Richard A. Castellano; DNL Zito Castellano (57) ABSTRACT

An interdental cleaning member includes a brush having a plurality of bristles, each of the plurality of bristles comprising a bristle shaft, the bristle shaft extending from a shaft base to a shaft tip, and formed to have a thickness and resiliency configured to clean interdental areas and areas interposing a tooth and gum tissue surrounding the tooth.

15 Claims, 7 Drawing Sheets

(56) References Cited

U.S. PATENT DOCUMENTS

| | | |
|---|---|---|
| 6,546,586 B2 | 4/2003 | Cho |
| 6,574,820 B1 | 6/2003 | Depuydt et al. |
| 6,735,804 B2 | 5/2004 | Carlucci |
| 6,760,946 B2 | 7/2004 | Depuydt |
| 7,311,108 B2 | 12/2007 | Getgey et al. |
| 7,421,753 B2 | 9/2008 | Chan |
| 7,448,107 B2 | 11/2008 | Depuydt |
| 7,832,042 B2 | 11/2010 | Depuydt |
| 7,941,886 B2 | 5/2011 | Chenvainu et al. |
| 8,011,057 B2 | 9/2011 | Nejat |
| 8,220,097 B2 | 7/2012 | Depuydt et al. |
| 8,539,630 B2 | 9/2013 | Gatzemeyer |
| 8,590,546 B2 | 11/2013 | Pruett |
| 2001/0004871 A1 | 6/2001 | Blaustein et al. |
| 2002/0039720 A1* | 4/2002 | Marx ............ A61C 17/26 433/216 |
| 2002/0059685 A1* | 5/2002 | Paffrath ............ A46B 9/04 15/28 |
| 2003/0182743 A1 | 10/2003 | Gatzemeyer et al. |
| 2005/0102776 A1 | 5/2005 | Mathur |
| 2005/0268409 A1 | 12/2005 | Blaustein et al. |
| 2007/0294847 A1 | 12/2007 | Wang |
| 2009/0029323 A1 | 1/2009 | Nejat |
| 2015/0216639 A1 | 8/2015 | Gottlieb |
| 2015/0216640 A1 | 8/2015 | Gottlieb |

OTHER PUBLICATIONS

International Preliminary Report on Patentability for International Application No. PCT/US2014/067193, dated Apr. 14, 2015, 4 pages.

Notification of Transmittal of Translation of the International Preliminary Report on Patentability (Chapter I or Chapter II) along with Written Opinion of the International Searching Authority for International Application No. PCT/US2014/067193, dated Apr. 14, 2015, 8 pages.

PCT/US2014/057928, Jan. 5, 2015, International Search Report and Written Opinion of International Searching Authority.

* cited by examiner

BRUSHES USEFUL FOR CLEANING TEETH AND INTERDENTAL SPACES

FIELD

The disclosure generally relates to oral hygiene tools. In particular, the disclosure relates to brushes, bristles, and bristle sets for cleaning teeth and interdental spaces.

BACKGROUND

As is known, a toothbrush is an oral hygiene instrument that is useful for cleaning teeth and gums. Conventional toothbrushes may include one or more heads of bristles that are arranged for cleaning the oral cavity—particularly, the teeth, tongue, and gums. Toothpaste is typically an abrasive fluid, paste, or gel dentifrice, and is used with toothbrushes to enhance cleaning by mechanical action. The cleaning effectiveness of toothbrushes has also been enhanced by using different bristle textures, sizes, and forms. In the past century, conventional toothbrushes have been modified to include soft bristles to protect tooth enamel and minimize gum damage and/or irritation, and may be formed of nylon or other materials that have desirable hardness and durability.

Some conventional toothbrushes are powered by electricity. An electric toothbrush includes a brush that is driven by a motor and oscillates or rotates the brush. Electric toothbrushes have been found to be easier to use than brushes that require completely manual brushing action. Moreover, electric toothbrushes have been clinically proven to generally be more effective for cleaning teeth than unpowered toothbrushes.

Other types of conventional toothbrushes include interdental or interproximal brushes and end-tufted brushes. Interdental cleaning instruments such as interdental brushes are designed for cleaning between teeth, and between braces and teeth. An interdental cleaning instrument may have a cleaning head that has a tapered surface profile. For example, a head of an interdental cleaning instrument may have a conical shape for cleaning the narrow spaces between teeth. An interdental cleaning instrument may alternatively include a brush having bristles located about a slender rod that is suitable for reaching between teeth to clean interdental spaces.

End-tufted toothbrushes are designed for cleaning along gumlines adjacent to teeth. End-tufted toothbrushes typically include a bristle head that is shaped to form an angled cleaning surface that conforms to interdental spaces. Dental instruments are conventionally required to perform specific dedicated cleaning functions for which they are narrowly suitable. Thus, an improved multi-functional electric toothbrush configured for easier, more effective, and more comprehensive tooth and interdental space cleaning was desired.

A powered multi-function brush configured for simultaneous cleaning of flat tooth surfaces and interdental spaces has been provided, however, by R. Gottlieb as disclosed in U.S. Patent Application Publication No. 2015/0216640, titled MUTLI-FUNCTION ELECTRIC BRUSH APPARATUS AND SYSTEMS USEFUL FOR CLEANING TEETH AND INTERDENTAL SPACES, published on Aug. 6, 2015, the entire disclosure of which is hereby incorporated by reference herein. Gottlieb discloses multi-function brushes useful for orthodontic, pedodontic, and periodontal applications, and may enable enhanced subgingival cleaning. In particular, Gottlieb discloses a powered dental and interdental cleaning tool including a body, an interdental cleaning member, and a drive member. The drive member may extend from the body at an angle to a longitudinal axis of the body. The drive member may be connected to the interdental cleaning member. A neck may extend from the body and define a drive member shaft for containing and supporting the drive member.

Further, an electric interdental cleaning apparatus and systems useful for cleaning teeth and interdental spaces has been provided by R. Gottlieb as disclosed in U.S. Patent Application Publication No. 2015/0216639, titled ELECTRIC INTERDENTAL CLEANING APPARATUS AND SYSTEMS USEFUL FOR CLEANING TEETH AND INTERDENTAL SPACES, published on Aug. 6, 2015, the entire disclosure of which is hereby incorporated by reference herein. Gottlieb discloses electric interdental cleaning devices configured for easier, more effective, and more comprehensive interdental space cleaning, and particularly for orthodontic, pedodontal, periodontal, and enhanced subgingival cleaning applications. In particular, Gottlieb discloses a powered dental and interdental cleaning tool including a body, an interdental cleaning member, and a drive member. The drive member extends from the body at an angle to a longitudinal axis of the body. The drive member is connected to the interdental cleaning member. A neck extends from the body and defines a drive member shaft for containing and supporting the drive member.

Conventional bristles and brushes are designed for tooth surface cleaning and relatively superficial cleaning of spaces between teeth and gums. Enhanced brushes suitable for reaching and cleaning interdental spaces and areas below gumlines may be beneficial generally, and particularly for use with electric teeth and interdental cleaning apparatus and systems such as those disclosed by Gottlieb.

SUMMARY

A need for enhanced bristles, bristle sets, and brushes useful for cleaning teeth and interdental spaces has been recognized. For example, a need for bristles, bristles sets, and brushes useful for powered multi-functional electric brush apparatus and systems and powered electric interdental cleaning apparatus and systems useful for cleaning teeth and interdental spaces has been recognized. Certain embodiments of the present invention may provide solutions to the problems and needs in the art that have not yet been fully identified, appreciated, or solved by current dental cleaning technologies. For example, in some embodiments of the present invention, a powered multi-function brush advantageously enables an apparatus useful for interdental cleaning, including an interdental cleaning member, the interdental cleaning member comprising a plurality of bristles, each of the plurality of bristles comprising a bristle shaft, the bristle shaft extending from a shaft base to a shaft tip, and formed to have a thickness and resiliency configured to clean interdental areas and areas interposing a tooth and gum tissue surrounding the tooth.

Additional features and technical effects of the present disclosure will become readily apparent to those skilled in the art from the following detailed description wherein embodiments of the present disclosure are described simply by way of illustration of the best mode contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF THE DRAWINGS

The present disclosure is illustrated by way of example, and not by way of limitation, in the figures of the accompanying drawing and in which like reference numerals refer to similar elements and in which.

DETAILED DESCRIPTION

In the following description, for the purposes of explanation, numerous specific details are set forth in order to provide a thorough understanding of exemplary embodiments. It should be apparent, however, that exemplary embodiments may be practiced without these specific details or with an equivalent arrangement. In other instances, well-known structures and devices are shown in block diagram form in order to avoid unnecessarily obscuring exemplary embodiments. In addition, unless otherwise indicated, all numbers expressing quantities, ratios, and numerical properties of ingredients, reaction conditions, and so forth used in the specification and claims are to be understood as being modified in all instances by the term "about".

The present disclosure addresses and solves the current problems attendant upon cleaning teeth and interdental spaces. Some embodiments of the present invention pertain to brushes for a powered multi-function device and for a powered interdental cleaning device that enable simultaneous cleaning of flat tooth surfaces and interdental spaces. The brushes are useful for orthodontic, pedodontal, and periodontal applications, and may enable enhanced subgingival cleaning under the gumline. For example, the brushes are configured for reaching and effectively and safely cleaning approximately 3 to 5 millimeters below the gumline, and preferably for cleaning at about 5 millimeters below the gumline.

Still other aspects, features, and technical effects will be readily apparent to those skilled in this art from the following detailed description, wherein preferred embodiments are shown and described, simply by way of illustration of the best mode contemplated. The disclosure is capable of other and different embodiments, and its several details are capable of modifications in various obvious respects. Accordingly, the drawings and description are to be regarded as illustrative in nature, and not as restrictive.

Figure 1A:
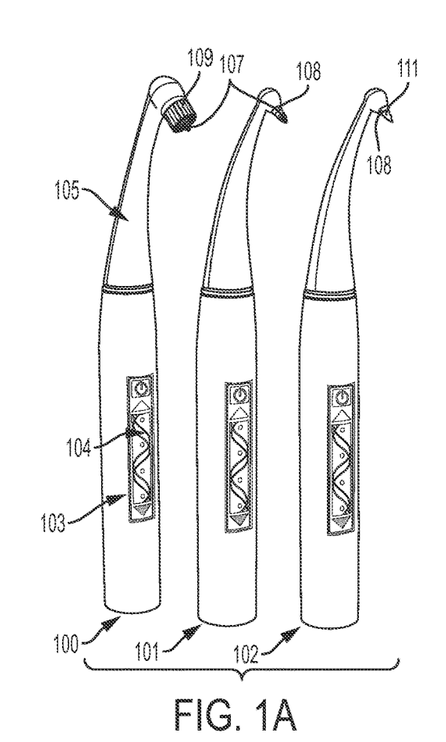
FIG. 1A shows a front perspective view of a multi-functional electric tooth and interdental space cleaning device, and electric interdental cleaning devices including brushes in accordance with an exemplary embodiment.

FIG. 1A shows a front perspective view of a multi-functional electric tooth and interdental space cleaning device, and electric interdental cleaning devices including brushes in accordance with an exemplary embodiment. In particular, FIG. 1A shows a multi-function electric device 100, an electric cleaning device 101 having a brush in accordance with an embodiment, and an interdental cleaning device 102 having a brush in accordance with another embodiment. Each of the multi-functional tooth and interdental cleaning device 100, and interdental cleaning devices 101, and 102 includes a body 103, and a neck and head 105.

FIG. 1A shows that a control panel 104 may be disposed on or within the body 103. The control panel may include a graphical and tactile user interface configured to enable powering on and off, controlling brush rotation and reciprocation speed, and understanding a power level, including a battery level, for example.

A drive member (not shown) may extend from a motor disposed within the body 103 through the neck to the head. The drive member may drive rotation and reciprocation of a toothbrush and interdental cleaning member. For example, FIG. 1A shows an interdental cleaning member 107 disposed to reciprocate axially from the head attached to the neck 105 of the multi-functional tooth and interdental space cleaning device 100, and the interdental cleaning device 101. Both interdental cleaning members 107 include concentrically disposed bristle sets arranged in progressively smaller, stepped rings, each having progressively taller bristles toward a center of the rings and together forming a point. Each of the bristles may be formed of a flexible, resilient material, now known or later developed, and useful for cleaning teeth and withstanding associated wear while causing minimal risk of tooth or tissue damage by abrasion, structural failure, or otherwise.

Each of devices 101 and 102 include a brush support 108 that configured for receding within the head. The interdental member 107 brush support of the multi-function device 100 is obscured by an outer tooth cleaning brush 109. The brush 109 may be configured for rotation along with rotation and reciprocation of the interdental cleaning member brush 107.

The interdental cleaning device 102 includes an interdental cleaning member brush 111 in accordance with another embodiment. In particular, the interdental cleaning brush 111 includes slender pointed bristles that are arranged to form a denser point with less visible graduations as the bristle rings edges form a smooth slope to the point.

Figure 1B:
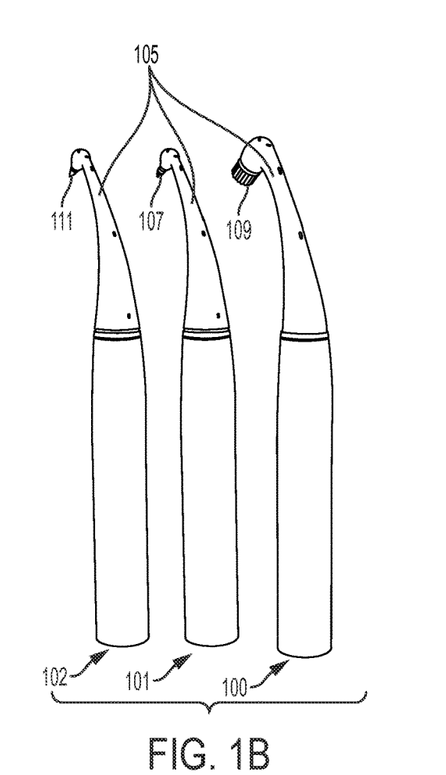
FIG. 1B shows a rear perspective view of a multi-functional electric tooth and interdental space cleaning device, and electric interdental cleaning devices including brushes in accordance with an exemplary.

FIG. 1B shows a rear perspective view of a multi-functional electric tooth and interdental space cleaning device, and electric interdental cleaning devices including brushes in accordance with an exemplary embodiment. In particular, FIG. 1B shows the multi-functional tooth and interdental cleaning device 100, and interdental cleaning devices 101, and 102 of FIG. 1A, each including a neck and head 105. FIG. 1B shows the multi-functional electric tooth and interdental space cleaning device 100 including an interdental cleaning member brush (not shown) and a tooth brush 109 surrounding the interdental cleaning member brush. The interdental cleaning device 101 includes an interdental cleaning member brush 107 including a stepped arrangement of concentric ringed bristle sets forming a point. The interdental cleaning device 102 includes an interdental cleaning member brush 111 including a sloping arrangement of concentric ringed bristle sets forming a point.

Figure 2:
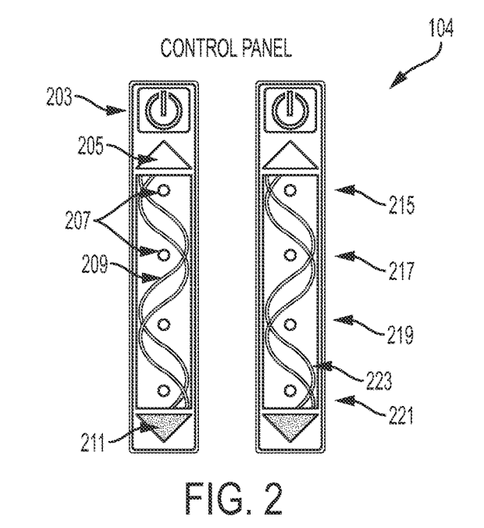
FIG. 2 shows a control panel of a multi-functional electric tooth and interdental space cleaning device, and electric interdental cleaning devices including brushes in accordance with an exemplary embodiment.

FIG. 2 shows a control panel of a multi-functional electric tooth and interdental space cleaning device, and electric interdental cleaning devices including brushes in accordance with an exemplary embodiment. FIG. 2 shows a control panel 104. The control panel 104 includes an on/off indicator and/or button 203, a speed increase indicator and/or button 205, battery level indicators and/or buttons 207, speed level indicators and/or buttons 209, and a speed decrease indicator and/or button 211.

FIG. 2 shows a control panel 104 that may include a touch sensitive film membrane, for example. The control panel may be backlit using a row of small LEDs that are arranged to emit light to pass through a masked printed surface. The battery level indicators and/or buttons 207 may be lit or dimmed to indicate, for example, a full battery signal 215, a high battery signal 217, a medium battery 219, or a low battery signal 221. A battery indicator and/or button 209 may be lit or dimmed, for example, to indicate a low speed signal 223.

Figure 3:
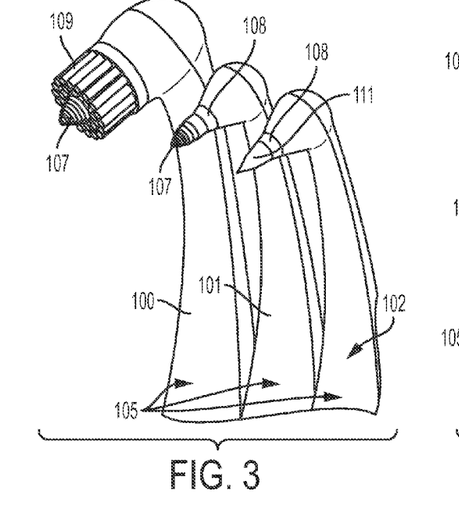
FIG. 3 shows an enlarged front perspective view of neck and head portions of a multi-functional electric tooth and interdental space cleaning device, and electric interdental cleaning devices including brushes in accordance with an exemplary embodiment.

FIG. 3 shows an enlarged front perspective view of neck and head portions of a multi-functional electric tooth and interdental space cleaning device, and electric interdental cleaning devices including brushes in accordance with an exemplary embodiment. In particular, FIG. 3 shows the multi-functional tooth and interdental cleaning device 100, and interdental cleaning devices 101, and 102, each including a neck and head 105. FIG. 3 shows the multi-functional electric tooth and interdental space cleaning device 100 including an interdental cleaning member brush 107 and a tooth brush 109 surrounding the interdental cleaning member brush. The interdental cleaning device 101 includes an interdental cleaning member brush 107 including a stepped arrangement of concentric ringed bristle sets forming a point. The interdental cleaning device 102 includes an interdental cleaning member brush 111 including a sloping arrangement of concentric ringed bristle sets forming a point.

Each of devices 101 and 102 include a brush support 108 that configured for receding within the head as the interdental cleaning member rotates and reciprocates axially in a pulsing movement. The interdental member 107 brush support of the multi-function device 100 is obscured by an outer tooth cleaning brush 109. The brush 109 may be configured for rotation along with rotation and reciprocation of the interdental cleaning member brush 107.

Figure 4:
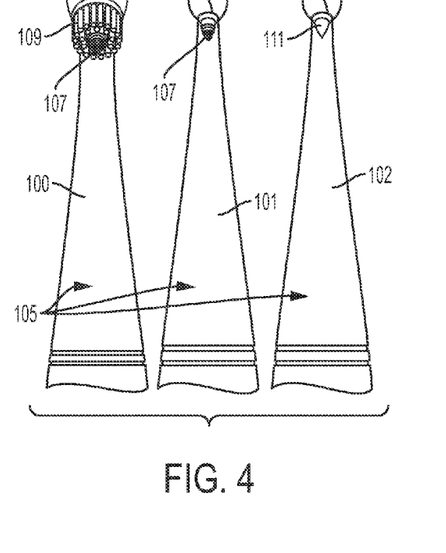
FIG. 4 shows an enlarged front view of neck and head portions of a multi-functional electric tooth and interdental space cleaning device, and electric interdental cleaning devices including brushes in accordance with an exemplary embodiment.

FIG. 4 shows an enlarged front view of neck and head portions of a multi-functional electric tooth and interdental space cleaning device, and electric interdental cleaning devices including brushes in accordance with an exemplary embodiment. In particular, FIG. 4 shows the multi-functional tooth and interdental cleaning device 100, and interdental cleaning devices 101, and 102, each including a neck and head 105. FIG. 4 shows the multi-functional electric tooth and interdental space cleaning device 100 including an interdental cleaning member brush 107 and a tooth brush 109 surrounding the interdental cleaning member brush. The interdental cleaning device 101 includes an interdental cleaning member brush 107 including a stepped arrangement of concentric ringed bristle sets forming a point. The interdental cleaning device 102 includes an interdental cleaning member brush 111 including a sloping arrangement of concentric ringed bristle sets forming a point.

Each of devices 101 and 102 include a brush support 108 that configured for receding within the head as the interdental cleaning member rotates and reciprocates axially in a pulsing movement. The interdental member 107 brush support of the multi-function device 100 is obscured by an outer tooth cleaning brush 109. The brush 109 may be configured for rotation along with rotation and reciprocation of the interdental cleaning member brush 107.

Figure 5:
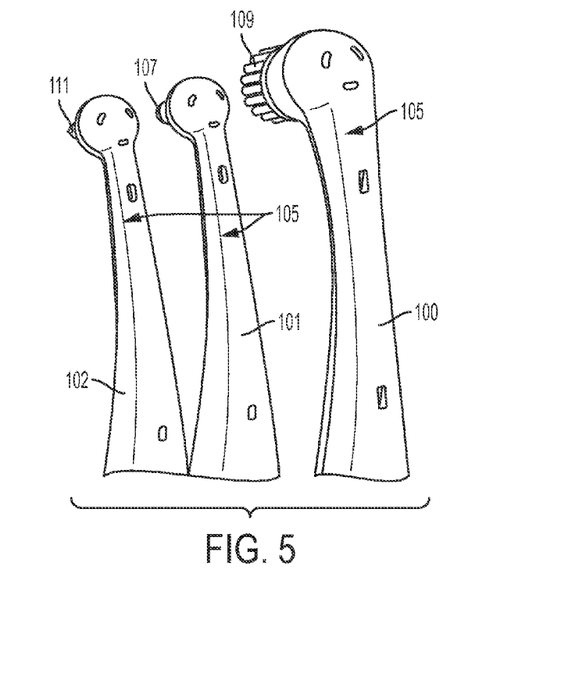
FIG. 5 shows an enlarged rear perspective view of neck and head portions of a multi-functional electric tooth and interdental space cleaning device, and electric interdental cleaning devices including brushes in accordance with an exemplary embodiment.

FIG. 5 shows an enlarged rear perspective view of neck and head portions of a multi-functional electric tooth and interdental space cleaning device, and electric interdental cleaning devices including brushes in accordance with an exemplary embodiment. FIG. 5 shows an enlarged rear perspective view of a multi-functional electric tooth and interdental space cleaning device, and electric interdental cleaning devices including brushes in accordance with an exemplary embodiment. In particular, FIG. 5 shows the multi-functional tooth and interdental cleaning device 100, and interdental cleaning devices 101, and 102 of FIG. 5, each including a neck and head 105. FIG. 5 shows the multi-functional electric tooth and interdental space cleaning device 100 including an interdental cleaning member brush (not shown) and a tooth brush 109 surrounding the interdental cleaning member brush. The interdental cleaning device 101 includes an interdental cleaning member brush 107 including a stepped arrangement of concentric ringed bristle sets forming a point. The interdental cleaning device 102 includes an interdental cleaning member brush 111 including a sloping arrangement of concentric ringed bristle sets forming a point.

Figure 6:
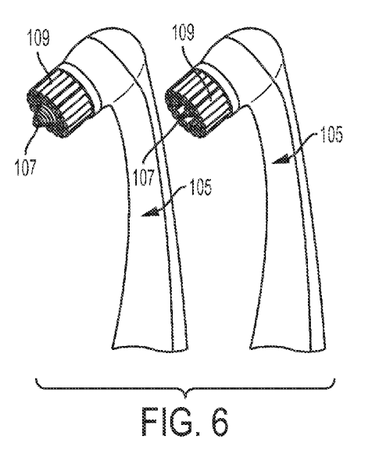
FIG. 6 shows an enlarged front perspective view of neck and head portions of a multi-functional electric tooth and interdental space cleaning device including brushes in accordance with an exemplary embodiment wherein the brushes are shown in retracted and extended positions.

FIG. 6 shows an enlarged front perspective view of neck and head portions of a multi-functional electric tooth and interdental space cleaning device including brushes in accordance with an exemplary embodiment wherein the brushes are shown in retracted and extended positions. In particular, FIG. 6 shows a multi-functional tooth and interdental cleaning device including a neck and head 105. FIG. 6 shows the multi-functional electric tooth and interdental space cleaning device including an interdental cleaning member brush 107 and a tooth brush 109 surrounding the interdental cleaning member brush. The interdental cleaning device includes an interdental cleaning member brush 107 including a stepped arrangement of concentric ringed bristle sets forming a point. The interdental cleaning member brush is configured to reciprocate with respect to the head, extending beyond the tooth brush 109 in an extended position, and retracted below a surface of the tooth brush 109 in a retracted position.

Figure 7:
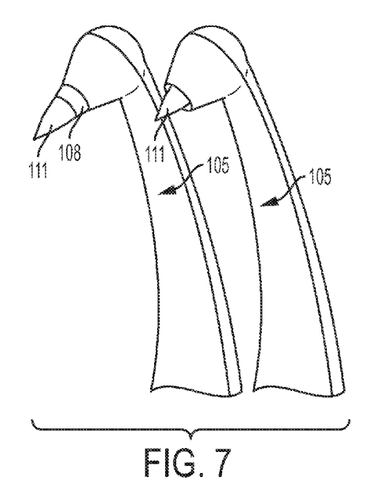
FIG. 7 shows an enlarged front perspective view of neck and head portions of a interdental space cleaning device including brushes in accordance with an exemplary embodiment wherein the brushes are shown in retracted and extended positions.

FIG. 7 shows an enlarged front perspective view of neck and head portions of an interdental space cleaning device including brushes in accordance with an exemplary embodiment wherein the brushes are shown in retracted and extended positions. In particular, FIG. 7 shows an interdental cleaning device including a neck and head 105. FIG. 7 shows the interdental cleaning device including an interdental cleaning member brush 111 supported by a brush support 108. The interdental cleaning member brush is configured to reciprocate with respect to the head, extending beyond the head outer surface in an extended position, and retracted below a surface of the head along with the brush support 108 in a retracted position. The brush support 108 and the brush 111 are configured for receding within the head as the interdental cleaning member rotates and reciprocates axially in a pulsing movement.

Figure 8:
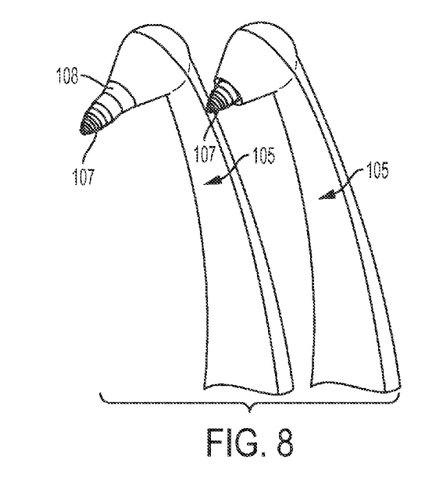
FIG. 8 shows an enlarged front perspective view of neck and head portions of a interdental space cleaning device including brushes in accordance with another exemplary embodiment wherein the brushes are shown in retracted and extended positions.

FIG. 8 shows an enlarged front perspective view of neck and head portions of an interdental space cleaning device including brushes in accordance with another exemplary embodiment wherein the brushes are shown in retracted and extended positions. In particular, FIG. 8 shows an interdental cleaning device including a neck and head 105. FIG. 8 shows the interdental cleaning device including an interdental cleaning member brush 107 supported by a brush support 108. The interdental cleaning member brush is configured to reciprocate with respect to the head, extending beyond the head outer surface in an extended position, and retracted below a surface of the head along with the brush support 108 in a retracted position. The brush support 108 and the brush 107 are configured for receding within the head as the interdental cleaning member rotates and reciprocates axially in a pulsing movement.

Figure 9:
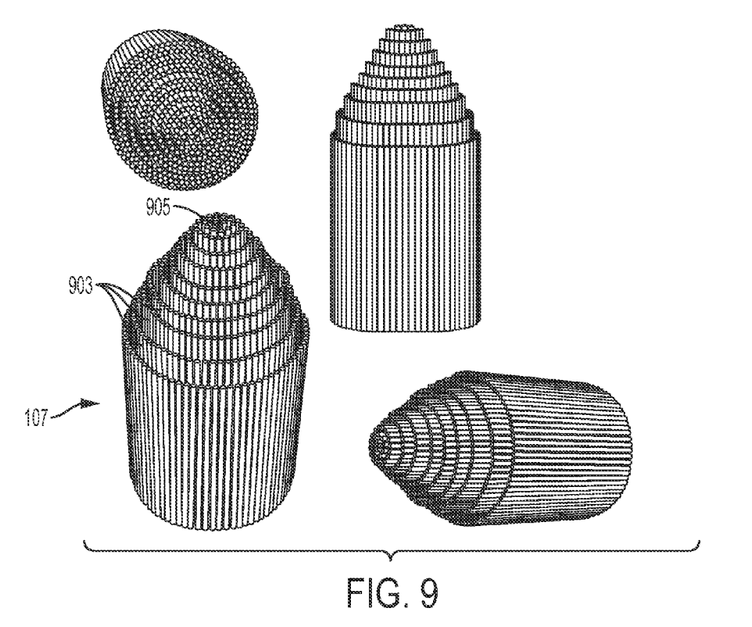
FIG. 9 shows a brush including concentrically arranged bristle sets in accordance with an exemplary embodiment.

FIG. 9 shows a brush including concentrically arranged bristle sets in accordance with an exemplary embodiment. In particular, FIG. 9 shows a brush 107 including concentrically arranged bristle sets 903 in the form of bristle rings. The ring bristle sets 903 are formed of cylindrical bristles that have substantially flat or planar or rounded ends or caps. The ring bristle sets 903 are concentrically arranged in a stepwise manner of increasing bristle height per ring unto a brush point 903. The bristles of the bristle sets 903 are formed of a material and configured and arranged so as to enable splaying and flexibility for form-fitting to structures and, to an extent, enabling deformation of the brush 107 to accommodate insertion of the brush 107 into narrow spaces and conformance of the brush 107 onto irregular structural surfaces. FIG. 9 shows front perspective, top, side, and side perspective views of the brush 107.

FIG. 10A-10E show brush and bristle sets in accordance with exemplary embodiments. FIGS. 10A-10C and 10E shows a brush 111 in accordance with an exemplary embodiment. The brush 111 formed of slender bristles that are tapered to a point toward a tip of the brush 111 to together form a dense and fine point 1005. The brush 111 includes concentrically arranged bristle sets in accordance with an exemplary embodiment. In particular, the brush 111 includes concentrically arranged bristle sets of bristles 1001 in the form of bristle rings. The ring bristle sets are formed of tapered bristles 1001 that have substantially pointed ends. The bristles 1001 are formed in concentrically arranged in a stepwise manner of increasing bristle height per ring unto a brush point 1005.

Figures 10A, 10B, 10C, 10D, 10E:
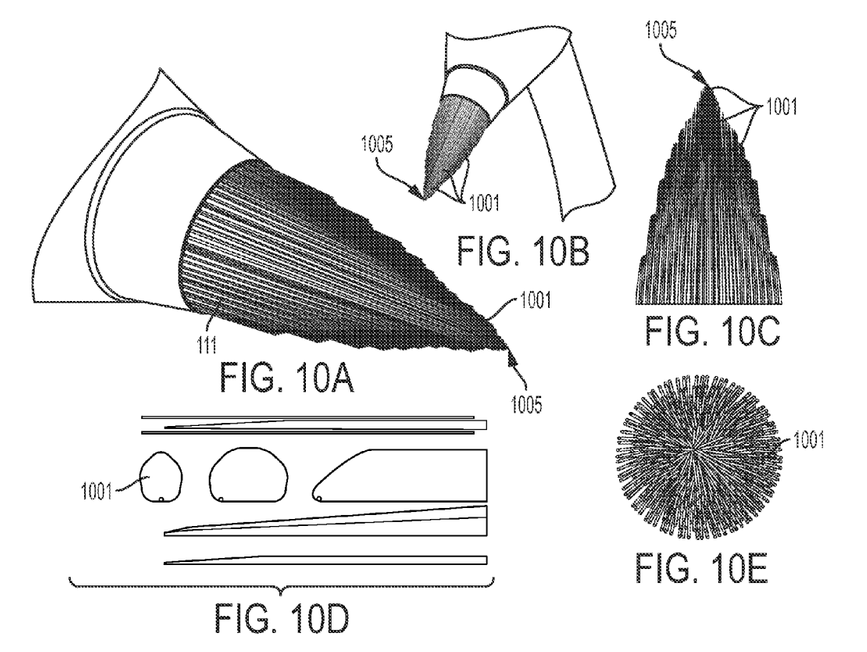
FIG. 10A-10E show brush and bristle sets in accordance with exemplary embodiments.

As shown in FIG. 10E, the bristles 1001 of the bristle sets are formed of a material and configured and arranged so as to enable splaying and flexibility for form-fitting to structures and, to an extent, enabling deformation of the brush 111 to accommodate insertion of the brush 111 into narrow spaces and conformance of the brush 111 onto irregular structural surfaces. As shown in FIG. 10D, the bristles 1001 are formed to taper to a point.

Figure 11:
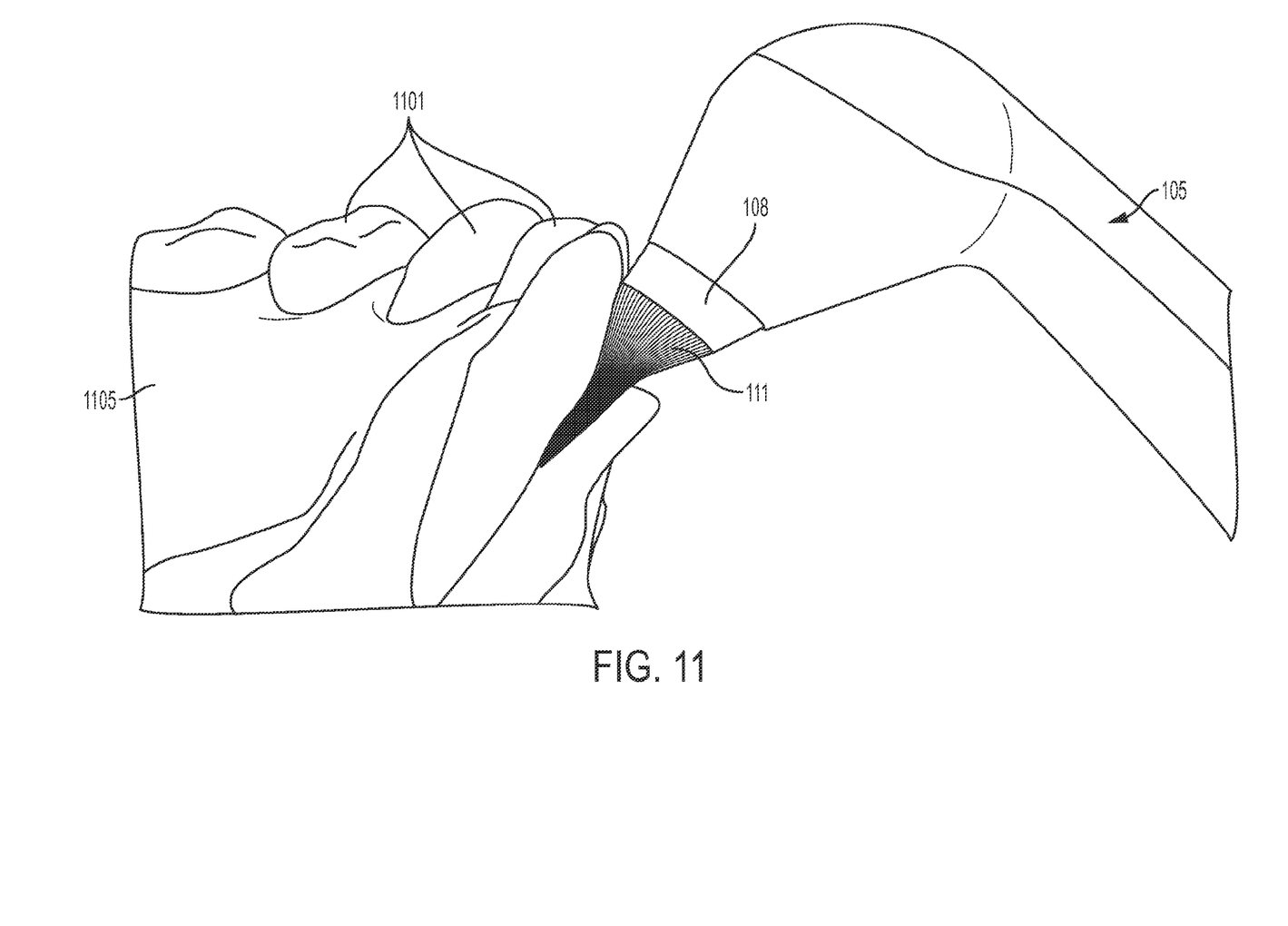
FIG. 11 shows an electric interdental cleaning device including a brush in accordance with an exemplary embodiment used for cleaning under gum lines and teeth.

FIG. 11 shows an electric interdental cleaning device including a brush in accordance with an exemplary embodiment used for cleaning between gums and teeth. In particular, FIG. 11 shows a head 105 of an interdental cleaning device having a brush 111 supported by a brush support 108 for rotation and axial reciprocation for cleaning, with respect to the head 105. The brush 111 and brush support 108 are shown in an extended position in FIG. 11. The brush 111 is shown inserted between teeth 1101 and gum tissue 1105 along movable and cleanable portions thereof.

Figure 12:
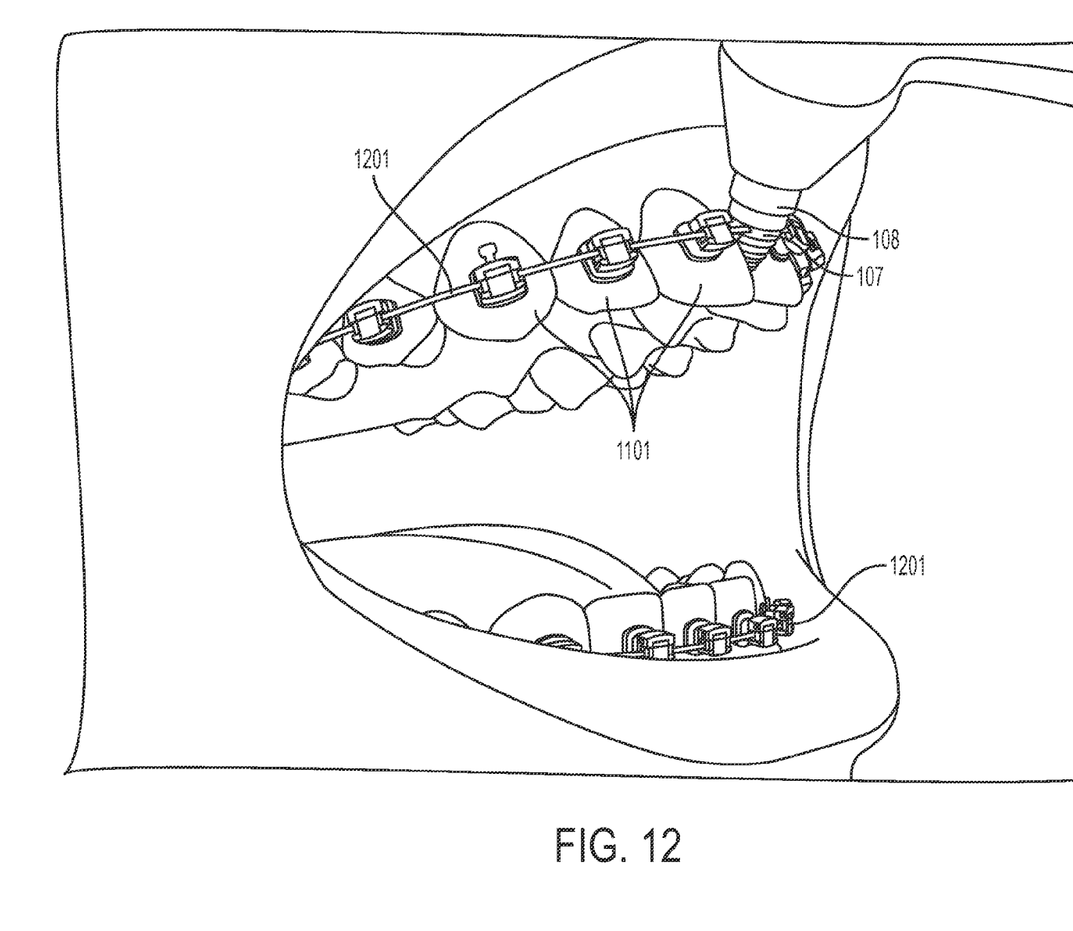
FIG. 12 shows a multi-functional tooth and interdental space cleaning device including a brush configuration in accordance with an exemplary embodiment cleaning a surface of teeth while cleaning interdental spaces.

FIG. 12 shows an interdental space cleaning device including a brush configuration in accordance with an exemplary embodiment cleaning a surface of teeth and cleaning interdental spaces. FIG. 12 shows an electric interdental cleaning device including a brush in accordance with an exemplary embodiment used for cleaning between gums and teeth. In particular, FIG. 12 shows an interdental cleaning device having a brush 107 supported by a brush support 108 for rotation and axial reciprocation for cleaning, with respect to the head. The brush 107 and brush support 108 are shown in an extended position in FIG. 12. The brush 107 is shown inserted between teeth 1101 and conforming to and being working around dental appliances 1201.

Figure 13:
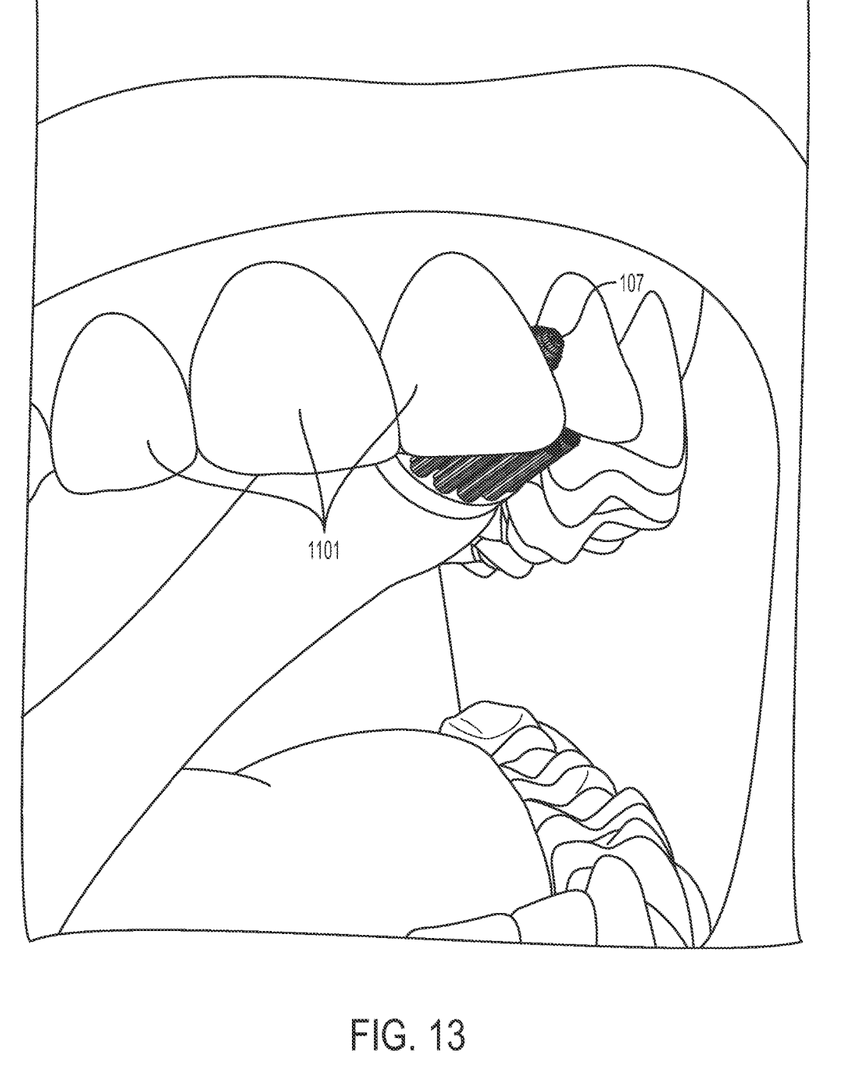
FIG. 13 shows a multi-functional tooth and interdental space cleaning device including a brush configuration in accordance with an exemplary embodiment cleaning a surface of teeth while cleaning interdental spaces.

FIG. 13 shows a multi-functional tooth and interdental space cleaning device including a brush configuration in accordance with an exemplary embodiment cleaning a surface of teeth while cleaning interdental spaces. FIG. 13 shows an electric interdental cleaning device including a brush in accordance with an exemplary embodiment used for cleaning between gums and teeth. In particular, FIG. 13 shows an interdental cleaning device having a brush 107 supported by a brush support for rotation and axial reciprocation for cleaning, with respect to the head. The brush 107 is shown in an extended position in FIG. 13. The brush 107 is shown inserted between teeth 1101 and conforming to and cleaning surfaces of teeth 1101 while a surrounding rotating brush cleans surfaces of teeth 1101 concurrently.

Accordingly, the brushes and brush configurations for multi-function tooth and interdental cleaning devices and interdental cleaning devices in accordance with embodiments advantageously enables simultaneous cleaning of flat tooth surfaces and interdental spaces or cleaning of teeth and interdental spaces. Further, the multi-function teeth and interdental cleaning device and the interdental cleaning device in accordance with some embodiments may be useful for many applications, including pedodontic, and orthodontic applications.

The brushes in accordance with embodiments may be useful for periodontal applications, and may enable enhanced cleaning under the gumline. For example, the brushes in accordance with some embodiments may include an interdental cleaning member and brush that is configured to reach about 3 to 5 millimeters below the gumline for cleaning.

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. An apparatus useful for interdental cleaning, comprising:
   an interdental cleaning member brush, the interdental cleaning member brush comprising a plurality of bristles, each of the plurality of bristles comprising a bristle shaft, the bristle shaft extending from a shaft base of the bristle to a shaft tip of the bristle, and formed to have a thickness and resiliency configured to clean interdental areas and areas interposing a tooth and gum tissue surrounding the tooth;
   an outer brush configured to surround the interdental cleaning member brush and configured to clean a tooth surface; an outer brush support supporting the outer brush and surrounding the interdental cleaning member, wherein the outer brush support and the interdental cleaning member are configured and arranged to enable the interdental cleaning member to rotate and reciprocate axially through an opening defined by the outer brush support.

2. The apparatus of claim 1, wherein the interdental cleaning member is configured to extend about 5 millimeters below a gumline of a user during use.

3. The apparatus of claim 1, wherein the interdental cleaning member is configured to extend about 1 centimeter beyond an opening of the outer brush support at a fully extended position.

4. The apparatus of claim 1, an interdental cleaning member brush support configured to support the interdental cleaning member brush.

5. The apparatus of claim 1, wherein the outer brush support is fixed and non-rotatable.

6. The apparatus of claim of claim 1, comprising:
   a head, the head defining an opening, wherein the interdental cleaning member brush is configured and arranged to rotate and reciprocate axially through the opening of the head.

7. The apparatus of claim 6,
   wherein the interdental cleaning member brush is configured to retract beneath an outer surface of the head.

8. The apparatus of claim 7, wherein the interdental cleaning member brush is configured to extend 5 millimeters beyond an opening of the head at a non-extended position.

9. The apparatus of claim 7, wherein the interdental cleaning member brush is configured to extend about 1 centimeter beyond an opening of the head at a fully extended position.

10. The apparatus of claim 1, comprising:
    a drive assembly configured to rotate the interdental cleaning member brush and cause pulsing movement of the interdental cleaning member brush.

11. The apparatus of claim 1, comprising:
    a body comprising a first end and a second end;
    a drive member extending from the first end of the body at an angle to a longitudinal axis of the body, the drive member connected to the interdental cleaning member brush;
    a neck comprising a first end and a second end, the neck extending from the first end of the body at the first end of the neck to a head comprising the interdental cleaning member brush, the neck defining a drive member shaft that contains the drive member, wherein the drive member extends from the body at an angle of about 20 degrees; and
    a variable speed motor connected to and configured to drive the drive member.

12. The apparatus of claim 1, wherein the plurality of bristles are angled to form a point.

13. The apparatus of claim 1, wherein the plurality of bristles are arranged in concentric rings, each of the concentric rings of bristles having different heights, the heights graduating to a point at a center of the plurality of bristles and stepped.

14. The apparatus of claim 13, wherein the bristle shaft is tapered to a point at the shaft tip.

15. The apparatus of claim 13, wherein the bristle shaft is substantially cylindrical along the shaft tip.

* * * * *